United States Patent
Juchno et al.

(10) Patent No.: US 10,219,839 B2
(45) Date of Patent: Mar. 5, 2019

(54) CLOSED-HEAD POLYAXIAL AND MONAXIAL SCREWS

(71) Applicant: GLOBUS MEDICAL, INC., Audubon, PA (US)

(72) Inventors: Brad Juchno, Yardley, PA (US); Milan George, King of Prussia, PA (US)

(73) Assignee: GLOBUS MEDICAL, INC., Audubon, PA (US)

(*) Notice: Subject to any disclaimer, the term of this patent is extended or adjusted under 35 U.S.C. 154(b) by 0 days.

(21) Appl. No.: 15/225,177

(22) Filed: Aug. 1, 2016

(65) Prior Publication Data

US 2016/0338739 A1 Nov. 24, 2016

Related U.S. Application Data

(63) Continuation of application No. 13/409,209, filed on Mar. 1, 2012, now Pat. No. 9,427,260.

(51) Int. Cl.
*A61B 17/86* (2006.01)
*A61B 17/70* (2006.01)

(52) U.S. Cl.
CPC ........ *A61B 17/704* (2013.01); *A61B 17/7001* (2013.01); *A61B 17/7037* (2013.01); *A61B 17/8625* (2013.01)

(58) Field of Classification Search
CPC ............ A61B 17/7091; A61B 17/7037; A61B 17/704; A61B 17/7001; A61B 2017/0425; A61B 2017/0453; F16B 35/044; F16B 41/002
See application file for complete search history.

(56) References Cited

U.S. PATENT DOCUMENTS

| | | | |
|---|---|---|---|
| 4,636,121 A * | 1/1987 | Miller | F16B 39/04 411/140 |
| 5,429,639 A * | 7/1995 | Judet | A61B 17/7005 403/362 |
| 5,672,176 A | 9/1997 | Biedermann | |
| 5,879,350 A | 3/1999 | Sherman | |
| 5,882,350 A | 3/1999 | Ralph | |
| 5,931,621 A * | 8/1999 | Griffith | F16B 39/02 411/255 |
| 6,063,090 A | 5/2000 | Schlapfer | |
| 6,074,391 A | 6/2000 | Metz-Stavenhagen | |
| 6,248,105 B1 | 6/2001 | Schlapfer et al. | |
| RE39,089 E | 5/2006 | Ralph | |
| 7,081,117 B2 | 7/2006 | Bono et al. | |
| 7,186,255 B2 | 3/2007 | Baynham et al. | |
| 7,308,312 B1 | 12/2007 | Lim | |
| D564,097 S | 3/2008 | Olerud | |

(Continued)

FOREIGN PATENT DOCUMENTS

| | | | |
|---|---|---|---|
| WO | 1998052482 A1 | 11/1998 | |
| WO | 2005018490 A2 | 3/2005 | |
| WO | 2007064632 A1 | 6/2007 | |

*Primary Examiner* — David W Bates

(57) ABSTRACT

A closed-head polyaxial screw for use in spinal instrumentation for spinal fusion, treatment of deformity, or the like. Polyaxial screws may have a two-part design, with the screw fitting into an aperture in the closed head. One or more clamps may secure the bone screw in the aperture. A closed-head polyaxial screw having a one part design is also disclosed. In addition, a one-part monaxial screw is described.

20 Claims, 6 Drawing Sheets

(56) References Cited

U.S. PATENT DOCUMENTS

| | | | |
|---|---|---|---|
| 7,789,900 B2 | 9/2010 | Levy | |
| 8,221,471 B2* | 7/2012 | Kovach | A61B 17/7032 606/266 |
| 8,241,341 B2 | 8/2012 | Walker et al. | |
| 8,282,675 B2* | 10/2012 | Maguire | A61B 17/8038 411/103 |
| 8,308,782 B2 | 11/2012 | Jackson | |
| 8,444,681 B2 | 5/2013 | Jackson et al. | |
| 8,876,874 B2 | 11/2014 | Abdou | |
| 8,979,898 B2 | 3/2015 | Ark et al. | |
| 9,028,498 B2* | 5/2015 | Hershgold | A61B 17/7059 606/71 |
| 9,068,587 B2* | 6/2015 | Sage | F16B 35/005 |
| 2005/0228385 A1 | 10/2005 | Iott et al. | |
| 2005/0234452 A1* | 10/2005 | Malandain | A61B 17/7007 606/54 |
| 2006/0009770 A1* | 1/2006 | Speirs | A61B 17/8047 606/287 |
| 2006/0149240 A1 | 7/2006 | Jackson | |
| 2007/0049933 A1 | 3/2007 | Ahn | |
| 2007/0093819 A1 | 4/2007 | Albert | |
| 2007/0118123 A1* | 5/2007 | Strausbaugh | A61B 17/7032 606/272 |
| 2007/0162029 A1 | 7/2007 | Whitmore | |
| 2007/0288004 A1* | 12/2007 | Alvarez | A61B 17/7032 606/86 A |
| 2008/0015579 A1 | 1/2008 | Whipple | |
| 2008/0015580 A1 | 1/2008 | Chao | |
| 2008/0045953 A1* | 2/2008 | Garamszegi | A61B 17/7032 606/86 A |
| 2008/0140136 A1 | 6/2008 | Jackson | |
| 2008/0294202 A1* | 11/2008 | Peterson | A61B 17/7032 606/305 |
| 2009/0163962 A1* | 6/2009 | Dauster | A61B 17/7032 606/305 |
| 2009/0182384 A1 | 7/2009 | Wilcox et al. | |
| 2009/0240290 A1 | 9/2009 | Choi | |
| 2010/0152787 A1 | 6/2010 | Walsh | |
| 2010/0160980 A1 | 6/2010 | Walsh | |
| 2010/0198272 A1 | 8/2010 | Keyer | |
| 2010/0234893 A1 | 9/2010 | Iott et al. | |
| 2010/0234902 A1 | 9/2010 | Biedermann | |
| 2010/0241175 A1 | 9/2010 | Walker et al. | |
| 2010/0256681 A1 | 10/2010 | Hammer | |
| 2011/0040335 A1 | 2/2011 | Stihl | |
| 2011/0152949 A1 | 6/2011 | Biedermann | |
| 2011/0160779 A1 | 6/2011 | Schlaepfer | |
| 2011/0196430 A1 | 8/2011 | Walsh | |
| 2011/0208251 A1 | 8/2011 | Hammill, Sr. et al. | |
| 2011/0213424 A1 | 9/2011 | Biedermann | |
| 2011/0230915 A1 | 9/2011 | Anderson | |
| 2012/0303063 A1 | 11/2012 | Cahill et al. | |

* cited by examiner

CLOSED-HEAD POLYAXIAL AND MONAXIAL SCREWS

REFERENCE TO RELATED APPLICATIONS

The present application is a continuation application of U.S. patent application Ser. No. 13/409,209, filed Mar. 1, 2012, which is hereby incorporated by reference in its entirety.

BACKGROUND OF THE PRESENT DISCLOSURE

1. Field of the Present Disclosure

The present disclosure is directed to closed-head bone screws for securing spinal instrumentation. Both monaxial and polyaxial screws are described.

2. Related Art

Spinal instrumentation may be used to treat a variety of conditions, including injury and deformity due to trauma or congenital defect. Spinal instrumentation may also be used in a spinal fusion procedure to alleviate the difficulties caused by a damaged or herniated intervertebral disc. Spinal instrumentation typically includes a number of bone screws for attaching to individual vertebrae. The pedicle is a preferred attachment point because it is easily accessible from the back of the patient and it offers a great depth of cortical bone. Once the pedicle screws are in place, one or more rods are placed vertically, substantially parallel to the long axis of the spine, and connected to the pedicle screws. Each rod is usually connected to at least two screws, each of which is attached to a different vertebra. The entire construct serves to properly align and/or separate the vertebrae. It may be supplemented with bone grafts, bone cement, or the like, to promote healing, long-term stability, and the like.

Traditionally, spinal instrumentation was installed via open-back surgery. This type of procedure tended to cause extensive trauma to the patient, resulting in long and painful recovery times. In recent years, a shift has been made toward minimally invasive surgery techniques. In minimally invasive surgery, the surgeon makes only one to a few small incisions and uses special tools to insert devices, observe his progress, and perform other activities in the surgical site. Minimally invasive surgery techniques frequently result in much less injury to the patient and improved healing and recovery times.

The pedicle screws commonly used in instrumentation procedures utilize an open-head design to connect to the rods. This head has a flat base with an arm rising on either side, giving it a U-shaped profile. In a monaxial design, the bone screw itself may be inserted through an opening in the base and then inserted into the bone. The rod is placed between the upright portions of the open head, and a locking clamp, which connects to the upright portions, is placed over the rod to lock it in place. Polyaxial designs are similar, but the connection between the head and the screw allows the head to twist and rotate relative to the bone screw.

Open-head polyaxial and monaxial screws suffer from certain shortcomings. The size of the head scales with the size of the bone screw. In situations that call for a larger screw, the surgeon may need to make more or larger incisions to accommodate the larger profile of the open-head screw. Conversely, if the surgeon will not or cannot enlarge the incision, he may instead use a smaller screw that may not have the strength necessary for the particular application at hand. In addition, smaller polyaxial screws, with their smaller heads, may be able to achieve greater relative angles between the head and the screw than larger screws. This is another reason a surgeon might select a smaller screw that may not be perfectly suited for the particular task at hand. Furthermore, having to maintain stocks of screws and heads in a variety of sizes is cumbersome, costly, and error-prone.

Accordingly, there is a need for low-profile, high-strength polyaxial and monaxial bone screws.

SUMMARY OF THE PRESENT DISCLOSURE

The present disclosure meets the foregoing need using a closed-head design, which results in a significant reduce in size without compromising strength, and other advantages apparent from the discussion herein.

Accordingly, one aspect of the present disclosure describes a closed-head polyaxial screw that includes a set screw, a bone screw, a closed head, a clamp, and a wedge. The closed head has an upper aperture that is structured to receive the set screw. The closed head also has a lower aperture that is structured to receive the bone screw. The clamp is structured and located to retain the bone screw in the lower aperture of the closed head. The wedge is structured and located to seat the clamp in the lower aperture.

The bone screw may have a head, and the clamp may be structured and located to interface with the head of the bone screw in the lower aperture. The outer surface of the head of the bone screw may be textured, the inner surface of the clamp may be textured, or both surfaces may be textured. The bone screw may include dual bone threads. The closed head may be structured to receive a rod oriented at any one of a number of angles relative to the bone screw. The set screw may be configured to retain the rod within the closed head, and the set screw may press the rod against the wedge. The wedge may have a cutout configured to receive the rod. The set screw may include a lip that is structured and arranged to contact at least a portion of the closed head, thereby retaining the set screw in the upper aperture.

According to another aspect of the present disclosure, a closed-head polyaxial screw includes a set screw, a bone screw, a closed head, and a clamp. The closed head is integrally formed or constructed as one piece with the bone screw. The closed head includes an upper aperture that is structured to receive the set screw. The clamp is structured to be positioned within the closed head.

The closed head may be structured and arranged to receive a rod oriented at one or more angles, which may be selectable from a plurality of angles, relative to the bone screw. The set screw is structured and arranged to compress the clamp, thereby causing the clamp to retain the rod within the closed head. The set screw may include an indentation structured and arranged to interface with the clamp. The closed head may include an orientation tab that is structured and arranged to properly orient the clamp within the closed head. The clamp may have a substantially circular shape or a substantially spherical shape. The bone screw may include dual bone threads.

In yet another aspect of the present disclosure, a closed-head monaxial screw includes a set screw, a bone screw, a closed head, and a clamp. The closed head is integrally formed or constructed as one piece with the bone screw. The closed head includes an upper aperture that is structured and arranged to receive the set screw. The clamp is structured to be positioned under the set screw. The bone screw may include dual bone threads. The closed head may be structured and arranged to receive a rod.

Additional features, advantages, and aspects of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION OF THE PRESENT DISCLOSURE

Figure 1:
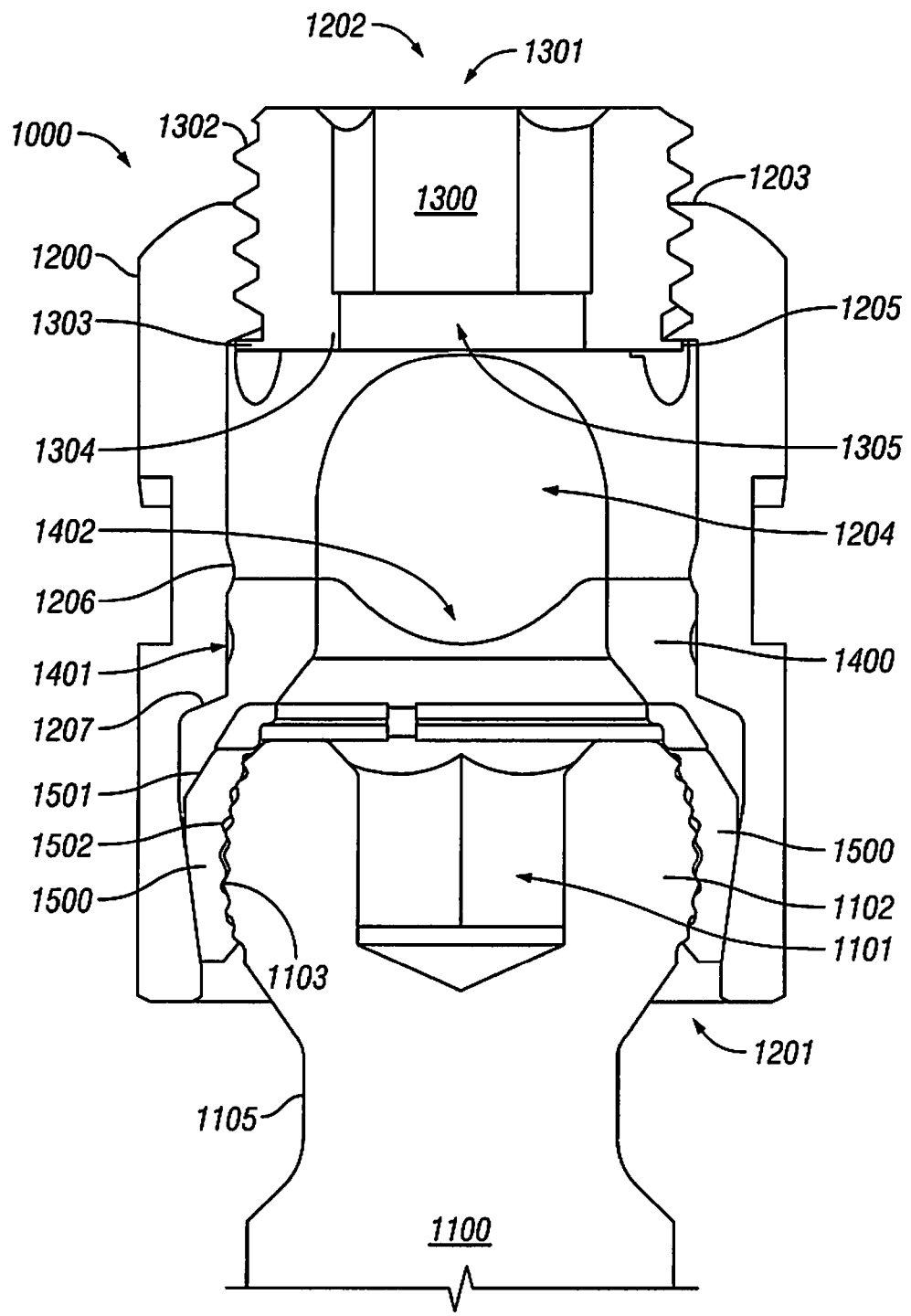
FIG. 1 shows a cutaway view of a closed-head polyaxial screw, according to an aspect of the present disclosure.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

FIG. 1 shows a cutaway view of a closed-head polyaxial screw 1000 according to an aspect of the present disclosure. The screw 1000 may include a bone screw 1100, a closed head 1200, a set screw 1300, a wedge 1400, and one or more clamps 1500. The closed head 1200 may include a lower aperture 1201, an upper aperture 1202, and a rod receiving aperture 1204. The rod receiving aperture 1204 may include an arch-shape with a semicircular top and vertical sides. This shape may present a maximum area, indicated by the semi-circular top, for a rod passing through or being retained within the screw 1000. For example, the rod may be moved toward the bone screw 1100 when the closed head 1200 is affixed to the rod, such as, e.g., by tightening the set screw 1300 onto the rod. The closed head 1200 may include a second rod receiving aperture 1204 so that a rod (not shown) may pass completely through the head 1200 rather than terminating in it.

The set screw 1300 may be introduced into the closed head 1200 through the lower aperture 1201. The upper aperture 1202 may be fitted with receiving threads 1203 for mating to threads 1302 on the set screw 1300. The set screw threads 1302 may be threaded onto the receiving threads 1203. The set screw 1300 may include a retaining lip 1303 or other modification (not shown) to prevent the set screw 1300 from being removed through the upper aperture of the closed head 1200. The lip 1303 may contact a rim or slope 1205 around the upper aperture 1202 to prevent the set screw 1300 from being threaded completely through the aperture 1202. The polyaxial screw 1000 may alternatively be structured to have the set screw 1300 threaded in from the top of the upper aperture 1202. These screws may have a lip 1303 to prevent the set screw 1300 from being threaded out the bottom of the aperture 1202 and into the middle of the closed head 1200.

The set screw 1300 may include a receiving socket 1301 for a tool, such as, e.g., a screw driver, a torx wrench, an allen wrench, a hex wrench, a socket driver, or the like. The base of the socket 1301 may include a rim 1304. When a tool (not shown) is inserted into the socket 1301, the rim 1304 may prevent the tool from being inserted past the set screw 1300 and into the interior space of the closed head 1200. When a rod (not shown) is inserted into or through the closed head 1200, the rim may prevent the tool from contacting and possibly damaging the rod. The rim 1303 may also define a cutout or hole 1305 at the center of the set screw. The cutout 1305 may be circular, hexagonal, or any other appropriate shape, and the cutout 1305 may allow a surgeon or other user of the polyaxial screw 1000 to view the progress of a rod as the rod is inserted into or through the closed head 1200.

The wedge 1400 may be inserted into the closed head 1200 through the lower aperture 1201 and pushed towards the upper aperture 1202. The wedge 1400 may include a groove 1401 that may mate to a ring 1206 located in the closed head 1200. The groove 1401 and the ring 1206 may interact to position and/or orient the wedge 1400 during assembly of the polyaxial screw 1000. The groove 1401 and the ring 1206 may also be structured to prevent the wedge 1400 from rising or being pushed above the point where the ring 1206 fits into the groove 1401. The wedge 1400 may include a cutout 1402, which may have a rounded shape. The cutout 1402 may mate to or receive a rod (not shown) inserted through the aperture 1204. For example, the rod may be pressed down into the cutout 1402 by the set screw 1300. The pressure or force of the rod on the wedge 1400 may seat the wedge 1400 onto one or more clamps 1500. The wedge 1400 may also transfer force or pressure to the clamps 1500, thereby increasing the pressure or friction of the interface between the clamps 1500 and the bone screw 1100, as discussed below.

One or more clamps 1500 may be inserted into the closed head 1200 through the lower aperture 1201. Each clamp 1500 may be circular, or it may occupy only a portion of the circumference of, e.g., the head of the bone screw 1100. For example, each clamp 1500 may be semicircular, or each may represent one-third of a circle, as seen in FIG. 1. The clamps 1500 may be centered or positioned so that they form a ring or circle. The clamps 1500 may then be pushed or moved towards the upper aperture 1202. A top tapered surface 1501 on each clamp may contact a tapered shoulder 1207 within the closed head 1200. As the clamps 1500 are pushed from below, the angle of the surface 1501 and/or the shoulder 1207 may cause the clamps 1500 to angle in toward each other. The clamps 1500 may come to a stop once each clamp 1500 comes into contact with another clamp 1500. This configuration and procedure may produce a wider opening at the bottom of the clamps 1500 than may be possible without the tapered surface 1501, tapered shoulder 1207, or both.

A bone screw 1100 may be inserted into the closed head 1200 through the lower aperture 1201. The bone screw 1100 may be inserted once the wedge 1400 and clamps 1500 are in position, so that the head 1102 of the bone screw may be surrounded by the clamps 1500 inside the closed head 1200. The bone screw 1100 may be manipulated or adjusted to ensure that the clamps 1500 are centered or properly positioned around the head 1102. Once the clamps 1500 are in position, the bone screw 1100 may be moved lower in the closed head 1200, which may seat the clamps 1500 lower in the head 1200, such as, e.g., seen in FIG. 1.

The position and orientation of the closed head 1200 may be adjusted by pressing the head 1200 along its longitudinal axis in the direction of the bone screw 1100, or moving the bone screw 1100 along the longitudinal axis of the closed head 1200 in the direction of the set screw 1300. This motion may loosen the connection between the head 1102 of the bone screw 1100 and the clamps 1500. With the clamps 1500 loosened, the closed head 1200 may be rotated, twisted, or moved relative to the bone screw 1100. Once the closed head 1200 is properly positioned, the connection between the head 1200 and the bone screw 1100 may be tightened by moving the closed head 1200 along its longitudinal axis in a direction away from the bone screw 1100, or moving the bone screw 1100 along the longitudinal axis of the closed head 1200 in a direction away from the set screw 1300.

The connection may be further strengthened or tightened by moving the wedge 1400 toward or onto the clamps 1500. The wedge may be moved toward the clamp(s) 1500 by, for example, compression. For example, a tool or other instrument (not shown) may be inserted through the rod receiving aperture 1204 and used to compress the wedge 1400. The force of the tool may be supplemented by rotating the set screw 1300 to further compress the tool and the wedge 1400. Similarly, a rod (not shown) may be inserted through the aperture 1204. The set screw 1300 may be used to hold the rod in place. Since the aperture 1204 is arch-shaped, a counter-force to the set screw 1300 may not be provided by the closed head 1200. Instead, the counter-force may be supplied by the wedge 1400, which may be supported by the clamps 1500 and the head 1102 of the bone screw 1100. Thus, using the set screw 1300 to lock a rod in position in the closed head 1200 may also lock the orientation of the closed head 1200 relative to the bone screw 1100.

The inner surface 1502 of one or more clamps 1500 may be textured or patterned, and the outer surface 1103 of the head 1102 of the bone screw 1100 may likewise be textured or patterned. The texture or pattern may include ribs, ridges, grooves, cross-hatching, or the like. The texture or pattern on the inner surface 1502 may be complementary to the texture or pattern on the outer surface 1103. The texture or pattern on the inner surface 1502, the outer surface 1103, or both may act to improve the strength of the interface between the clamps 1500 and the head 1102 of the bone screw 1300, for example, by increasing the friction between the two surfaces. A stronger interface between the clamps 1500 and the head 1102 of the bone screw 1300 may result in a stronger connection between the bone screw 1300 and the closed head 1200, which in turn may improve the overall strength and stability of the spinal instrumentation.

The bone screw 1100 may include a receiving socket 1101 for receiving a tool, such as, e.g., a screw driver, a torx wrench, an allen wrench, a hex wrench, a socket driver, or the like. The socket 1101 may be sized so that a tool (not shown) may be inserted through the cutout 1305 in the set screw 1300 to actuate the bone screw 1100. As an alternative means of actuating or rotating the bone screw 1100, e.g., into bone, the screw 1100 may be locked relative to the closed head 1200 as described above, then a special tool (not shown) may interface with the closed head 1200 and rotate the head 1200, thereby rotating the screw 1100. The tool may also interface with both the closed head 1200 and the bone screw 1100. As a third option, the bone screw 1100 may be inserted into a suitable site, e.g., a vertebral pedicle. The closed head 1200 may be assembled with the set screw 1300, wedge 1400, and clamps 1500 and attached to the screw 1100 once the screw 1100 is in position. This technique may make it easier for a surgeon to properly insert the screw 1100 into the site. With this technique, the screw 1100 may be fixed in place, and the other components of the polyaxial screw 1000 may move relative to it. For example, when it is described that the bone screw 1100 may be inserted into the lower aperture 1201, this motion is relative. It should be understood that the screw 1100 may be fixed in position, and the aperture 1201 may be fitted over or onto the screw head 1102. This distinction will be clear and easily understood by those skilled in the art.

The bone screw 1100 may include one or more bone threads. For example, the screw 1100 may have dual bone threads (as seen, e.g., in FIGS. 4 and 5). Dual bone threads may increase the purchase of the screw in both cortical bone and cancellous bone. The increased purchase may, in turn, reduce or substantially eliminate toggling, loosening, or pulling out of the bone screw 1100.

Figure 2:
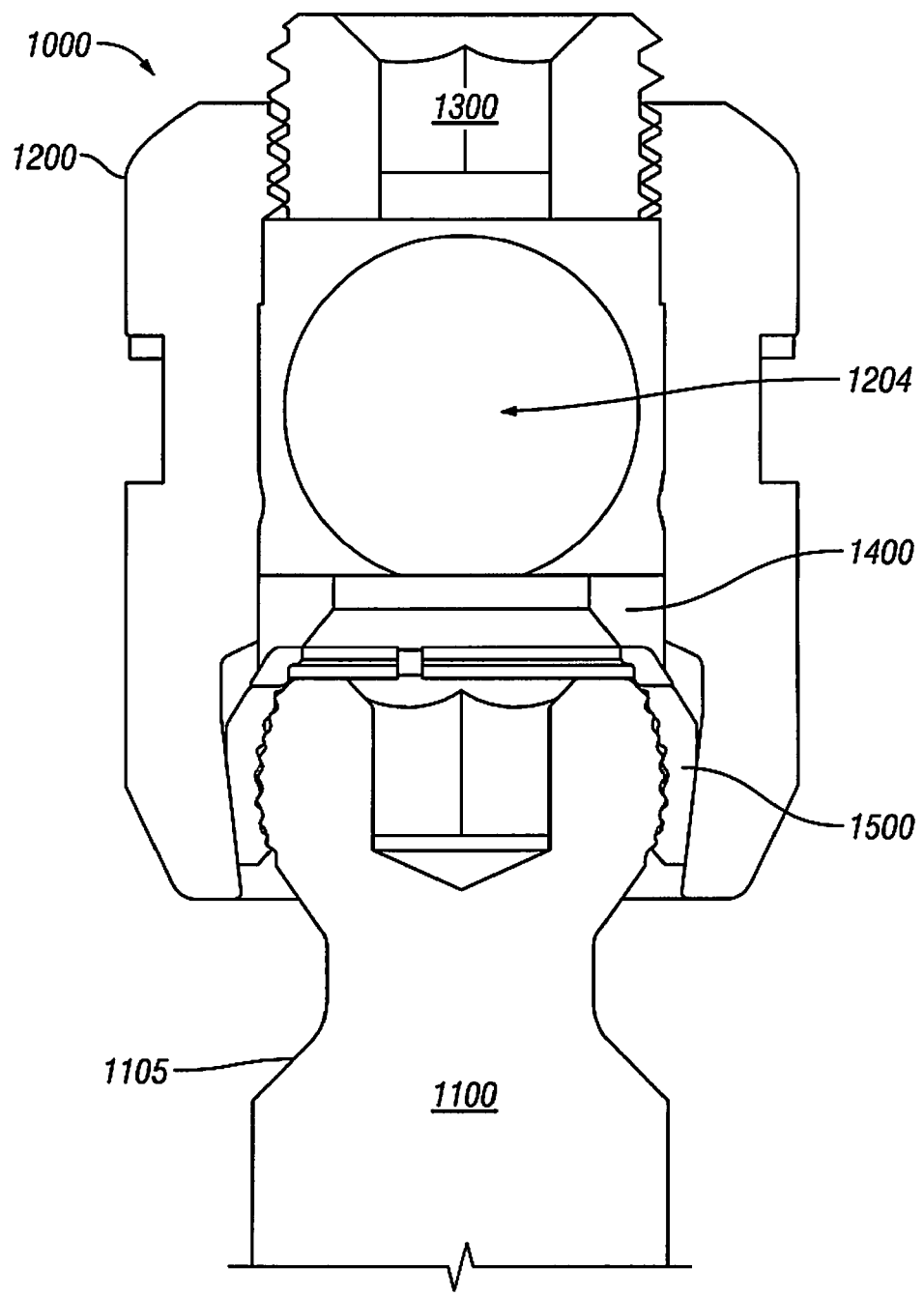
FIG. 2 shows a closed-head polyaxial screw, according to an alternate aspect of the present disclosure.

FIG. 2 shows a closed-head polyaxial screw 1000 according to an alternate aspect of the present disclosure. The rod receiving aperture 1204 may be circular, and the wedge 1400 may have a flat upper surface. The wedge 1400 may overlap with the aperture 1204, so that inserting a rod (not shown) through the aperture 1204 may apply pressure to the wedge 1400 or force the wedge 1400 in the direction of the clamp(s) 1500. A force or pressure on the wedge 1400 may be passed to one or more clamps 1500, thereby increasing the pressure or friction of the interface between the clamps 1500 and the bone screw 1100. A set screw 1300 may be tightened onto a rod (not shown) inserted through the closed head 1200 to affix the closed head 1200 to the rod.

Figure 3:
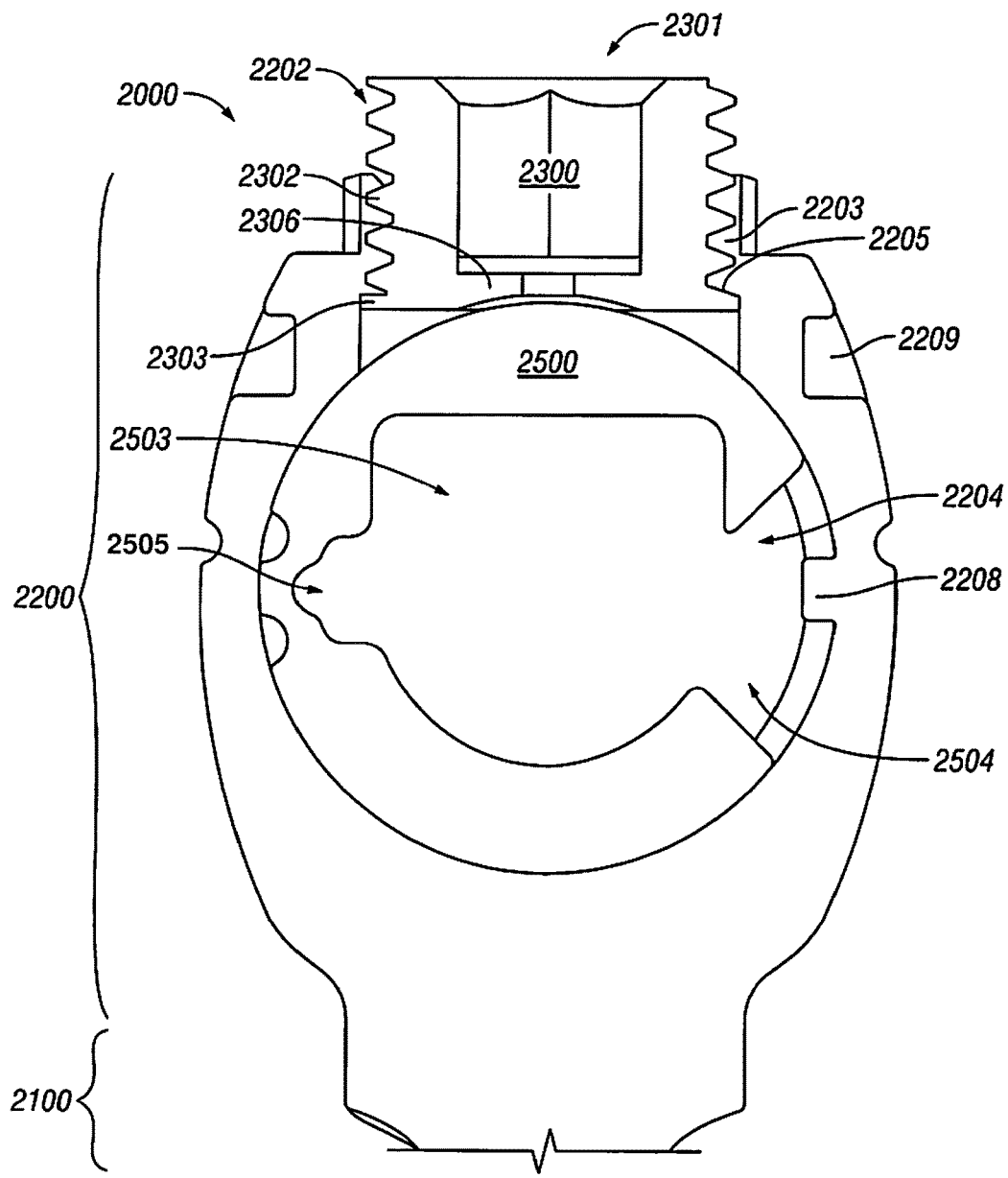
FIG. 3 shows a closed-head polyaxial screw according to a further aspect of the present disclosure.

FIG. 3 shows a closed-head polyaxial screw 2000 according to a further aspect of the present disclosure. The polyaxial screw 2000 may include a closed head 2200, which may be integrally formed with a bone screw 2100, a set screw 2300, and a clamp 2500. The closed head 2200 and the bone screw 2100 may be formed as one piece. The closed head may include an upper aperture 2202, as well as an aperture 2204 for receiving a rod or similar structure (not shown).

The set screw 2300 may include threads 2302. The set screw 2300 may be inserted into the aperture 2204. The set screw 2300 may be threaded onto receiving threads 2203 in the upper aperture 2202. The set screw 2300 may include a retaining lip 2303. As the set screw 2300 is threaded away from the bone screw 2100, through the upper aperture 2202, the lip 2303 may contact a rim or slope 2205 around the upper aperture 2202. The interaction between the lip 2303 and the rim 2205 may prevent the screw 2300 from being threaded out of the upper aperture 2202. The underside of the set screw 2300 may include an indentation 2306 that may be contoured to contact or mate with a clamp 2500, as discussed below.

The clamp 2500 may be inserted into the closed head 2200 by placing the clamp 2500 in a flat or sideways orientation and passing it through the aperture 2204. Once inside the closed head 2200, the clamp 2500 may be rotated or twisted into position. Proper positioning of the clamp 2500 may be assisted by an orientation tab 2208 located inside the closed head 2200, as seen, e.g., in FIG. 3. For example, the orientation tab 2208 may fit into an orientation gap 2504 in the clamp 2500. The clamp 2500 may include a circular, semi-circular, semi-spherical, or the like, shape. The clamp 2500 may include, for example, a c-clamp, or the like. The clamp 2500 may define a central opening 2503. The opening 2503 may have a shape that is circular, square, hexagonal, or the like, or any combination thereof. For example, the opening 2503 is seen in FIG. 3 as having an upper portion that may be square and a lower portion that may be circular. The clamp 2500 may be made of a biocompatible material. It may be somewhat soft and pliable, or it may be relative rigid.

The polyaxial screw 2000 may be inserted into bone using standard surgical techniques. A special tool may be used to drive the screw 2000, and the closed head 2200 may include one or more attachment points, sockets, or receivers 2209 for such a tool. A rod (not shown) may be inserted into the rod receiving aperture 2204 and through the opening 2503 in the clamp 2500. The set screw 2300 may the threaded toward or onto the clamp 2500, thereby compressing the clamp 2500. This compression may cause the clamp 2500 to change shape and make the opening 2503 smaller. For example, the set screw 2300 and the indentation 2306 may cause the top portion of the clamp 2500 to slide around the orientation gap 2504 until it abuts the orientation tab 2208. As the set screw 2300 continues to descend, the bottom portion of the clamp 2500 may slide into the orientation gap 2504 until it also abuts the orientation tab 2208. This controlled collapse of the clamp 2500 may be assisted by a cutout 2505 on the opposite side of the clamp 2500 from the orientation gap 2504.

The aperture 2204 and the clamp 2500 may be able to accommodate rods that are not perfectly perpendicular to the closed head 2200. For example, the clamp 2500 may be made of a more flexible material, and the opening 2503 may be wider that the rod. As the set screw 2300 is threaded toward or onto the clamp 2500, the clamp 2500 may be compressed and close around the rod and at least partially conform to the shape of the rod, thereby increasing the friction or otherwise strengthening the interface between the clamp and the rod. Additionally or alternatively, the outside of the clamp 2500 may be roughly circular, spherical, or cylindrical in shape, and it may be located in a substantially circular or spherical chamber within the closed head 2200. The clamp 2500 may be made of a substantially rigid material. As the set screw 2300 is threaded toward or onto the clamp 2500, the clamp 2500 may twist and rotate so that the opening 2503 is better aligned with the rod. As the clamp 2500 tightens around the rod, more of its surface may be in contact with the rod, thereby increasing the friction or otherwise strengthening the interface between the clamp and the rod.

Figure 4:
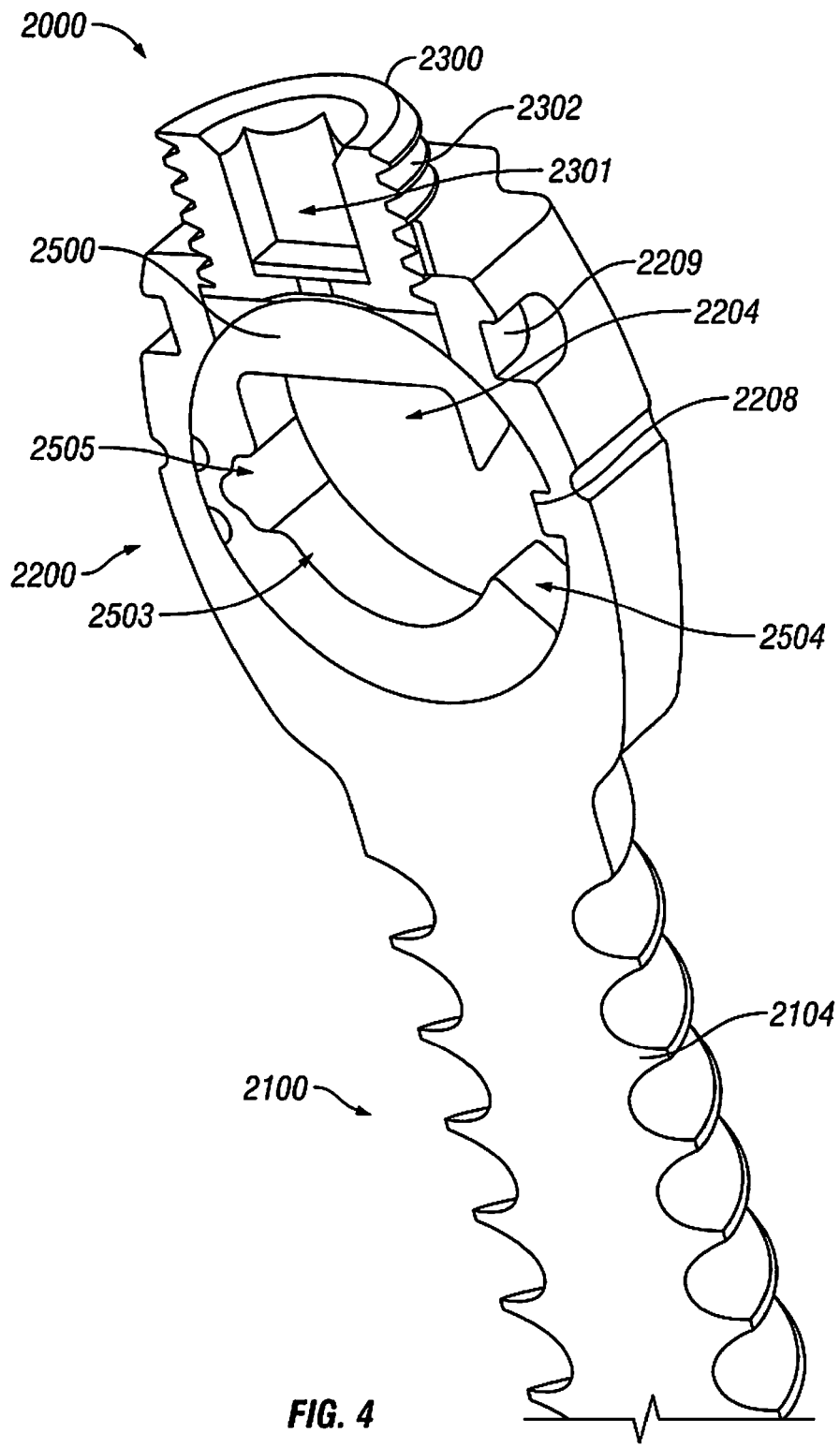
FIG. 4 shows a perspective view of the closed-head polyaxial screw of FIG. 3.

FIG. 4 shows a perspective view of the closed-head polyaxial screw 2000. The bone screw portion 2100 of the screw 2000 may include one or more bone threads 2104. For example, screws of the present disclosure may have two or more threads around their outer diameter. The use of multiple threads may improve the purchase of the screw in both cortical and cancellous bone, which may in turn reduce or substantially eliminate toggle and/or pull-out of the screw 2000.

Closed-head polyaxial screws of the present disclosure may offer one or more additional advantages. For example, a closed-head screw may be smaller than a comparable open-head design. A smaller size may make the screw more compatible with minimally invasive surgery techniques, such as, e.g., requiring a smaller incision. The lower aperture 1201 may accommodate bone screws 1100 of different sizes, or bone screws of different sizes may all be manufactured with heads 1102 that are compatible with the lower aperture 1201. Accordingly, only one size or type of closed head 1200 may need to be manufactured, which may result in lower manufacturing costs. Those savings may be passed on to healthcare providers and ultimately patients. A constant size of the neck 1105 and lower aperture 1201, regardless of screw size, may enable the possible angles between the closed head 1200 and the screw 1100 to be the same across all sizes of screw 1100. Possible angles between polyaxial screw 2000 and a rod (not shown) may likewise not be affected the by size of the bone screw 2100. By eliminating relative angle as a criterion for selecting screw size, polyaxial screws of the present disclosure may allow surgeons to select screws based on medical criteria rather than characteristics of the screw itself. Since polyaxial screw 1000 employs a bottom-loading design, the design may be used to make closed-head polyaxial hooks. The necessary changes and modifications will be apparent to those skilled in the art without departing from the spirit and scope of the present disclosure.

Figure 5:
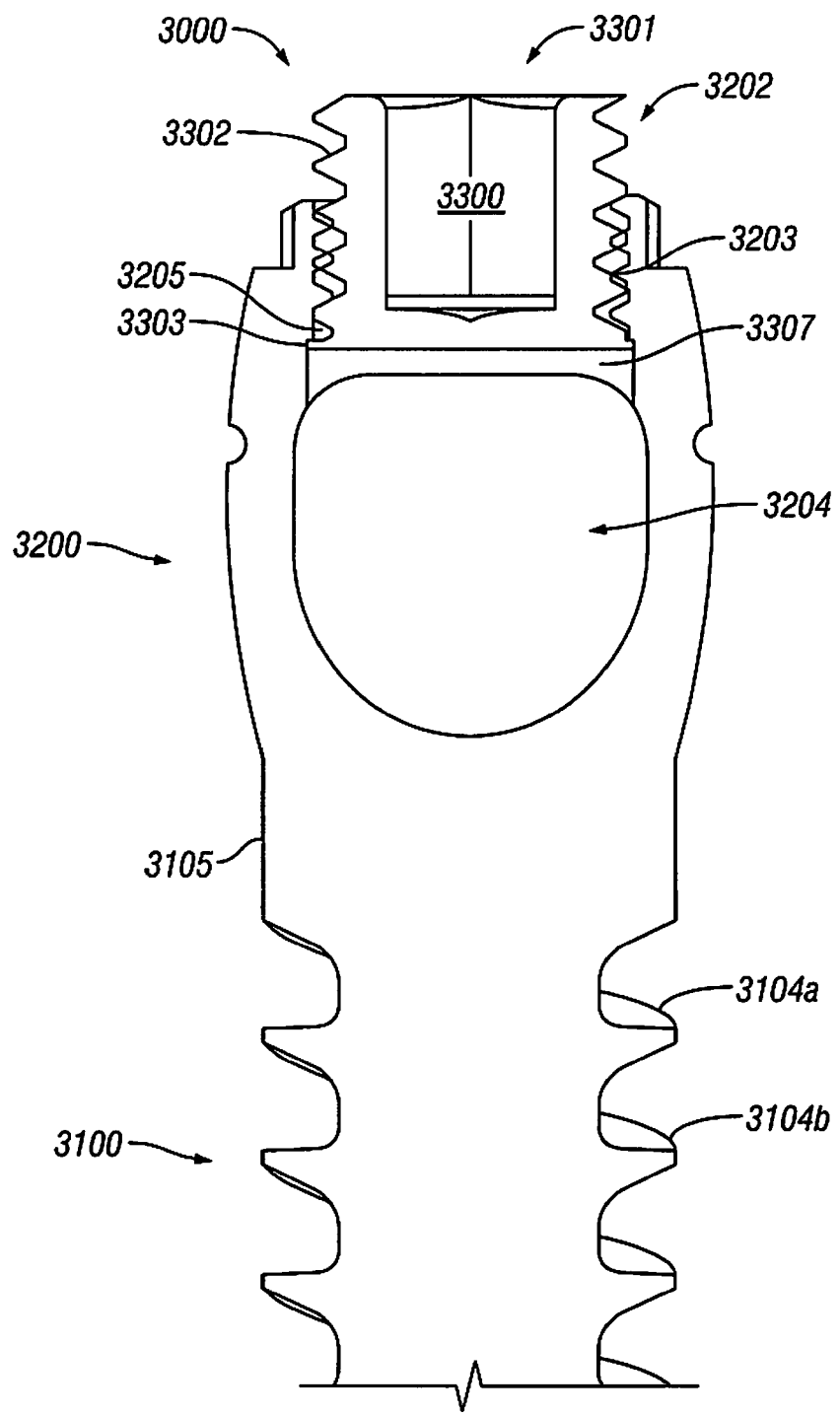
FIG. 5 shows a closed-head monaxial screw according to an aspect of the present disclosure.

FIG. 5 shows a closed-head monaxial screw 3000 according to an aspect of the present disclosure. The monaxial screw 3000 may include a bone screw 3100 integrally formed with a closed head 3200. The bone screw 3100 and the closed head 3200 may be formed using one-piece construction. A set screw 3300 may be located in the closed head 3200. The bone screw 3100 and the closed head 3200 may be connected by a neck 3105. The bone screw 3100 may have a plurality of threads, which may offer greater purchase and stability in both cortical and cancellous bone. Greater purchase and stability may reduce or substantially eliminate toggling and/or pulling out of the monaxial screw 3000. For example, the bone screw may have dual bone threads 3104*a*, 3104*b*, as seen in FIG. 5.

The closed head 3200 may include a rod receiving aperture 3204 and an upper aperture 3202. The set screw 3300 may be introduced through the rod receiving aperture 3204 and then threaded onto receiving threads 3203 in the upper aperture 3202. The receiving threads may mate with threads 3302 located on the outer surface of the set screw 3300. The set screw may include a lip 3303 that may contact a rim 3205 around the upper aperture. Interaction between the lip 3303 and the rim 3205 may prevent the set screw 3300 from being threaded out of the upper aperture 3202. The set screw 3300 may also include a socket 3301 for receiving a tool, such as, e.g., a screw driver, a torx wrench, an allen wrench, a hex wrench, a socket driver, or the like.

The monaxial screw 3000 may be inserted into bone using standard surgical techniques. A special tool may be necessary or provided to grip the closed head 3200 of the screw 3000 and twist the head 3200 to drive the screw 3000 into the bone. Once the monaxial screw 3000 is positioned in bone, a rod (not shown) may be inserted through the aperture 3204 in the head 3200. To affix the screw 3000 to the rod, a tool may be inserted into socket 3301 to rotate, thread, or drive the set screw 3300 towards the rod. The set screw 3300, in turn, may engage the rod. The set screw 3300 may include a rod interface surface 3307 made of a more flexible, biocompatible material. As the set screw 3300 is driven further and applies greater pressure to the rod, the surface 3307 may conform to the shape of the rod, resulting in a greater area of contact between the surface 3307 and the rod. The greater contact area, in turn, may increase the friction or strength of the interface between the surface 3307 and the rod.

The closed head design of the monaxial screw 3000 may result in a smaller size with fewer moving parts than an equivalent open-head screw. A smaller size may be more compatible with minimally invasive surgery techniques, e.g., by allowing a surgeon to use a smaller incision. The dual bone threads 3104a, 3104b, combined with a larger neck 3105 relative to the shank size, may provide more secure fixation to bone than with previous and/or open-head designs. More secure fixation may include, e.g., reduced or substantially eliminated chance of pullout, toggling, breakage, or other disruption of the connection between the screw 3000 and bone to which it is attached. In addition, the size of the closed head 3200 may remain constant while the diameter of the bone screw 3100 may vary, which may enable common instrumentation for all screw sizes. Common instrumentation may make surgical procedures faster and simpler. Furthermore, common instrumentation may reduce manufacturing and shipping costs, and these savings may be passed on to medical professionals and ultimately patients.

Figure 6:
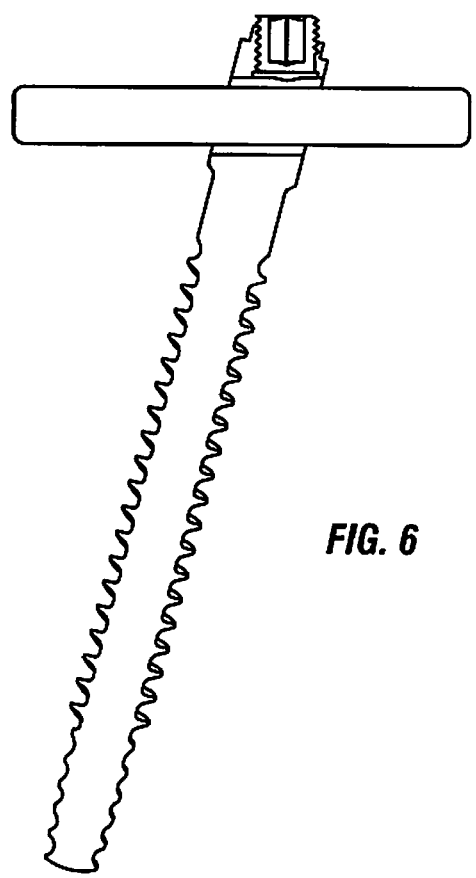
FIG. 6 shows a closed-head monaxial screw according to another aspect of the present disclosure.
Figure 7:
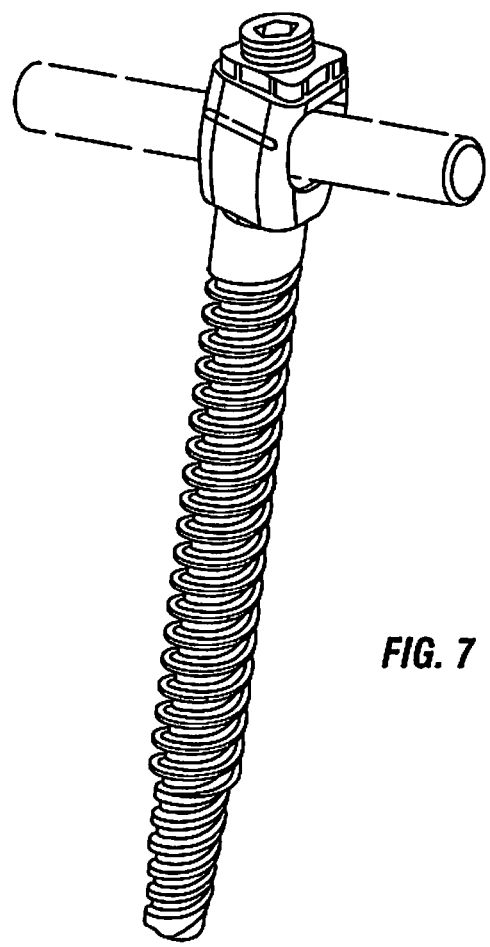
FIG. 7 shows a closed-head polyaxial screw according to the present disclosure.

FIGS. 6 and 7 illustrate another embodiment of the present invention. FIG. 6 shows a closed-head monoaxial screw having the angled tulip portion of the screw. The angulation of the closed-head tulip allows for the insertion of the elongate rod at an angle. FIG. 7 shows a closed-head polyaxial screw having an angled closed head tulip that also allows the rod to be positioned at an angle rather than being perpendicular to the head of the screw. It should be noted that although a single angled closed head tulip is illustrated, any angle that is suitable can be manufacture to accommodate for use in the spine. It should be further noted that the set screw on the angled closed-head mono and polyaxial screws are also angled so that the rod may be captured within optimally within the closed-head portion of the screw.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A closed-head polyaxial screw comprising:
a head member for receiving a rod therein;
a bone screw connected to the head member;
a C-shaped clamp positionable around the rod and having an integral body with an upper portion above the rod and a lower portion below the rod; and
a set screw extending through an aperture in the head member, wherein the set screw is prevented from moving upwardly and out of the aperture in the head member, wherein the set screw cannot be upwardly removed from the head member due to direct contact between the set screw and the head member, and wherein when the set screw is moved onto the clamp, the clamp is compressed to close around the rod.

2. The closed-head polyaxial screw of claim 1, wherein the head member and the bone screw are formed as one piece.

3. The closed-head polyaxial screw of claim 1, wherein the set screw comprises a retaining lip.

4. The closed-head polyaxial screw of claim 3, wherein the retaining lip is capable of contacting a rim of the head member for preventing the set screw from moving upwardly and out of the aperture of the head member.

5. The closed-head polyaxial screw of claim 1, wherein the clamp is insertable into the head member.

6. The closed-head polyaxial screw of claim 5, wherein the head member comprises an orientation tab protruding from an inner surface thereof.

7. The closed-head polyaxial screw of claim 6, wherein the clamp comprises an orientation gap such that the orientation tab can fit within the orientation gap.

8. The closed-head polyaxial screw of claim 5, wherein the clamp is compressible.

9. The closed-head polyaxial screw of claim 1, wherein the clamp is insertable into the head member, wherein the set screw extends downwardly onto the clamp.

10. The closed-head polyaxial screw of claim 9, wherein the clamp is compressible.

11. A closed-head polyaxial screw comprising:
a head member for receiving a rod therein;
a bone screw formed integrally with the head member;
a C-shaped clamp positionable around the rod and having an integral body with an upper portion above the rod and a lower portion below the rod; and
a set screw extending through an aperture in the head member, wherein the set screw is prevented from moving upwardly and out of the aperture in the head member, wherein the set screw cannot be upwardly removed from the head member due to direct contact between the set screw and the head member, and wherein when the set screw is moved onto the clamp, the clamp is compressed to close around the rod.

12. The closed-head polyaxial screw of claim 11, wherein the clamp is received in the head member, wherein the clamp comprises a circular opening.

13. The closed-head polyaxial screw of claim 11, wherein the set screw comprises a retaining lip.

14. The closed-head polyaxial screw of claim 13, wherein the retaining lip is capable of contacting a rim of the head member for preventing the set screw from moving upwardly and out of the aperture of the head member.

15. The closed-head polyaxial screw of claim 11, wherein the clamp insertable into the head member.

16. The closed-head polyaxial screw of claim 15, wherein the head member comprises an orientation tab protruding from an inner surface thereof.

17. The closed-head polyaxial screw of claim 16, wherein the clamp comprises an orientation gap such that the orientation tab can fit within the orientation gap.

18. The closed-head polyaxial screw of claim 15, wherein the clamp is compressible.

19. The closed-head polyaxial screw of claim 11, wherein the clamp is insertable into the head member, wherein the set screw extends downwardly onto the clamp.

20. The closed-head polyaxial screw of claim 19, wherein the clamp is compressible.

* * * * *